United States Patent
Kevlahan et al.

(10) Patent No.: US 10,739,338 B2
(45) Date of Patent: Aug. 11, 2020

(54) SHAPED ARTICLES INCLUDING HYDROGELS AND METHODS OF MANUFACTURE AND USE THEREOF

(71) Applicant: QT Holdings Corp, Beverly, MA (US)

(72) Inventors: Sean H. Kevlahan, Stoneham, MA (US); Brian D. Plouffe, Cumberland, RI (US); Jeffrey A. Zonderman, Westwood, MA (US)

(73) Assignee: QT Holdings Corp, Beverly, MA (US)

( * ) Notice: Subject to any disclaimer, the term of this patent is extended or adjusted under 35 U.S.C. 154(b) by 505 days.

(21) Appl. No.: 15/128,488

(22) PCT Filed: Mar. 24, 2015

(86) PCT No.: PCT/US2015/022256
§ 371 (c)(1),
(2) Date: Sep. 23, 2016

(87) PCT Pub. No.: WO2015/148512
PCT Pub. Date: Oct. 1, 2015

(65) Prior Publication Data
US 2017/0176428 A1 Jun. 22, 2017

Related U.S. Application Data

(60) Provisional application No. 61/969,448, filed on Mar. 24, 2014.

(51) Int. Cl.
*G01N 33/543* (2006.01)
*G01N 33/548* (2006.01)

(52) U.S. Cl.
CPC ..... *G01N 33/54366* (2013.01); *G01N 33/548* (2013.01); *G01N 33/54353* (2013.01)

(58) Field of Classification Search
CPC ........................... G01N 33/548; G01N 33/543
See application file for complete search history.

(56) References Cited

U.S. PATENT DOCUMENTS 6,352,694 B1    3/2002    June et al.
6,534,055 B1    3/2003    June et al.
(Continued)

FOREIGN PATENT DOCUMENTS

EP    2034009 A2    3/2009
EP    2177236 A1    4/2010
(Continued)

OTHER PUBLICATIONS

Hatch et al. (Engineered alginate hydrogels for effective microfluidic capture and release of endothelial progenitor cells from whole blood, Langmuir, vol. 27, pp. 4257-4264, published Mar. 14, 2011) (Year: 2011).*

(Continued)

*Primary Examiner* — Tracy Vivlemore
*Assistant Examiner* — Nam P Nguyen
(74) *Attorney, Agent, or Firm* — Casimir Jones, S.C.; Anne M. Reynolds

(57) ABSTRACT

The invention features shaped articles containing a structure and a hydrogel coating thereon, the hydrogel coating containing alginic acid conjugated to a polyalkylene oxide and a binding moiety. The hydrogel coating on the structure is sized and shaped to fit in a well in a microtiter plate and the coating does not cover the entire exterior of the surface. The invention further features methods of capturing targets using shaped articles and methods of preparing shaped articles.

28 Claims, 3 Drawing Sheets

(56) References Cited

U.S. PATENT DOCUMENTS

| | | | |
|---|---|---|---|
| 6,642,363 | B1 | 11/2003 | Mooney et al. |
| 7,204,139 | B2 | 4/2007 | Takayama |
| 7,214,245 | B1 | 5/2007 | Marcolongo et al. |
| 7,592,431 | B2 | 9/2009 | Har-Noy |
| 9,790,467 | B2* | 10/2017 | Kevlahan ............. C12N 5/0636 |
| 9,927,334 | B2 | 3/2018 | Murthy et al. |
| 2001/0051374 | A1 | 12/2001 | McLaughlin-Taylor et al. |
| 2003/0162164 | A1* | 8/2003 | Bochner ................ C12Q 1/18 435/4 |
| 2003/0235908 | A1 | 12/2003 | Berenson et al. |
| 2006/0094060 | A1 | 5/2006 | Jarhede et al. |
| 2006/0121012 | A1 | 6/2006 | Kutryk et al. |
| 2006/0141045 | A1 | 6/2006 | Bhatt et al. |
| 2007/0259424 | A1 | 11/2007 | Toner et al. |
| 2009/0041825 | A1 | 2/2009 | Kotov et al. |
| 2010/0144902 | A1 | 6/2010 | Shu |
| 2010/0261270 | A1 | 10/2010 | Peeters et al. |
| 2011/0144286 | A1 | 6/2011 | Wu |
| 2012/0061305 | A1 | 3/2012 | Quake et al. |
| 2012/0270209 | A1 | 10/2012 | Shah et al. |
| 2013/0017264 | A1 | 1/2013 | Khandare et al. |
| 2013/0315880 | A1 | 11/2013 | Frank |
| 2014/0057280 | A1 | 2/2014 | Murthy et al. |
| 2014/0154703 | A1 | 6/2014 | Skelley et al. |
| 2015/0030619 | A1 | 1/2015 | Milone et al. |
| 2015/0118318 | A1 | 4/2015 | Fahmy et al. |
| 2015/0160237 | A1 | 6/2015 | Wiencierz et al. |
| 2017/0081636 | A1 | 3/2017 | Kevlahan et al. |

FOREIGN PATENT DOCUMENTS

| | | |
|---|---|---|
| WO | WO-98/12228 A1 | 3/1998 |
| WO | WO-03/040235 A1 | 5/2003 |
| WO | WO-2006/020580 A2 | 2/2006 |
| WO | WO-2006/096746 A1 | 9/2006 |
| WO | WO-2009/074932 A1 | 6/2009 |
| WO | WO-2010/124227 A2 | 10/2010 |
| WO | WO-2011/078990 A1 | 6/2011 |
| WO | WO-2012/042467 A2 | 4/2012 |
| WO | WO-2012/106658 A1 | 8/2012 |
| WO | WO-2012/148684 A1 | 11/2012 |
| WO | WO-2013/188786 A1 | 12/2013 |
| WO | WO-2015/168379 A2 | 11/2015 |
| WO | WO-2017/161371 A1 | 9/2017 |
| WO | WO-2018/175408 A1 | 9/2018 |

OTHER PUBLICATIONS

Sigmaaldrich.com (print retrieved on Mar. 27, 2019). (Year: 2019).*
U.S. Appl. No. 16/086,267, Kevlahan et al.
Arya et al., "Capturing rare cells from blood using a packed bed of custom-synthesized chitosan microparticles," J Mater Chem B. 1(34): 4313-4319 (2013) (12 pages).
Cabodi et al., "A microfluidic biomaterial," J Am Chem Soc. 127(40):13788-9 (2005).
Pierzchalski et al., "An innovative cascade system for simultaneous separation of multiple cell types," PLoS One. 8(9): e74745 (2013) (9 pages).
Barker et al., "Identification of stem cells in small intestine and colon by marker gene Lgr5," Nature. 449(7165):1003-1007 (2007).
Barker et al., "The intestinal stem cell," Genes Dev. 22(14):1856-1864 (2008).
Bjerknes et al., "Intestinal epithelial stem cells and progenitors," Methods Enzymol. 419:337-383 (2006).
Casati et al., "Clinical-scale selection and viral transduction of human naïve and central memory CD8+ T cells for adoptive cell therapy of cancer patients," Cancer Immunol Immunother. 62(10): 1563-73 (2013).
Scoville et al., "Current View: Intestinal Stem Cells and Signaling," Gastroenterology. 134(3):849-864 (2008).
Fatin-Rouge et al., "Removal of some divalent cations from water by membrane-filtration assisted with alginate," Water Res. 40(6):1303-1309 (2006).
Flynn et al., "Stem memory T cells (TSCM)—their role in cancer and HIV immunotherapies," Clin Transl Immunology. 3(7): e20 (2014) (7 pages).
Gracz et al., "Sox9 expression marks a subset of CD24-expressing small intenstine epithelial cells that form organoids in vitro," Am J Physiol Gastrointest Liver Physiol. 298(5):G590-600 (2010).
Hatch et al., "Engineered Alginate Hydrogels for Effective Microfluidic Capture and Release of Endothelial Progenitor Cells from Whole Blood," available in PMC Apr. 5, 2012, published in final edited form as: Langmuir. 27(7):4257-64 (2011) (16 pages).
International Search Report and Written Opinion for International Application No. PCT/US15/22256, dated Jul. 1, 2015 (14 pages).
Levine et al., "Antiviral effect and ex vivo CD4+ T cell proliferation in HIV-positive patients as a result of CD28 costimulation," Science. 272(5270): 1939-43 (1996).
Levine et al., "Effects of CD28 costimulation on long-term proliferation of CD4+ T cells in the absence of exogenous feeder cells," J Immunol. 159(12): 5921-30 (1997).
Mahou et al., "Novel Alginate-Poly(ethylene glycol) Hydrogel for Immobilization and Delivery: Synthesis and Physical Properties Assessment," XVIIth Int. Conference on Bioencapsulation, Sep. 24-26, Groningen, Netherlands. pp. 1-4, Poster P63 (2009) (2 pages).
Montgomery et al., "Prominin1 (CD133) as an Intestinal Stem Cell Marker: Promise and Nuance," Gastroenterology. 136(7):2051-2054 (2009).
O'Connor et al., "Substrate rigidity regulates human T cell activation and proliferation," J Immunol. 189(3): 1330-9 (2012) (11 pages).
Olsen Hult et al., "EP Receptor Expression in Human Intestinal Epithelium and Localization Relative to the Stem Cell Zone of the Crypts," PLoS One. 6(10):e26816 (2011) (11 pages).
Plouffe et al., "Controlled capture and release of cardiac fibroblasts using peptide-functionalized alginate gels in microfluidic channels," Lab Chip. 9(11):1507-10 (2009).
Rasmussen et al., "Ex vivo expansion protocol for human tumor specific T cells for adoptive T cell therapy," J Immunol Methods. 355(1-2): 52-60 (2010).
Sangiorgi et al., "Bmi1 is expressed in vivo in intestinal stem cells," available in PMC Jul. 19, 2010, published in final edited form as: Nat Genet. 40(7):915-20 (2008) (16 pages).
Sato et al., "Paneth cells constitute the niche for Lgr5 stem cells in intestinal crypts," available in PMC Jan. 17, 2013, published in final edited form as: Nature. 469(7330):415-18 (2011) (10 pages).
Sato et al., "Single Lgr5 stem cells build crypt-villus structures in vitrro without a mesencyhmal niche," Nature. 459(7244):262-5 (2009).
Sei et al., "A stem cell marker-expressing subset of enteroendocrine cells resides at the crypt base in the small intestine," Am J Physiol Gastrointest Liver Physiol. 300(2): G345-G356 (2011).
Snippert et al., "Prominin-1/CD133 Marks Stem Cells and Early Progenitors in Mouse Small Intestine," Gastroenterology. 136(7):2187-2194 (2009).
Sunshine et al., "Particle shape dependence of CD8+ T cell activation by artificial antigen presenting cells," available in PMC Jan. 1, 2015, published in final edited form as: Biomaterials. 35(1): 269-77 (2014) (17 pages).
Trickett et al., "T cell stimulation and expansion using anti-CD3/CD28 beads," J Immunol Methods. 275(1-2):251-5 (2003).
Tumeh et al., "The impact of ex vivo clinical grade activation protocols on human T cell phenotype and function for the generation of genetically modified cells for adoptive cell transfer therapy," available in PMC Oct. 1, 2011, published in final edited form as: J Immunother. 33(8):759-68 (2010) (17 pages).
Turtle et al., "CD19 CAR-T cells of defined CD4+:CD8+ composition in adult B cell All patients," J Clin Invest. 126(6): 2123-38 (2016).
Verbeke et al., "Multicomponent Injectable Hydrogels for Antigen-Specific Tolerogenic Immune Modulation," Adv Healthc Mater. (2017) (15 pages).
Williams et al., "Human T lymphocytes and hematopoietic cell lines express CD24-associated carbohydrate epitopes in the absence of CD24 mRNA or protein," Blood. 88(8): 3048-55 (1996).

(56) References Cited

OTHER PUBLICATIONS

Yamaguchi et al., "Polysaccharide-poly(ethylene glycol) star copolymer as a scaffold for the production of bioactive hydrogels," Biomacromolecules 6(4):1921-30 (2005).

* cited by examiner

SHAPED ARTICLES INCLUDING HYDROGELS AND METHODS OF MANUFACTURE AND USE THEREOF

BACKGROUND

The invention is generally directed to compositions and methods for separations and bioengineering.

Cellular isolation techniques are an essential component in studying specific populations, allowing for growth, genomic, and proteomic investigations. The detachment of cells adhered to any surface requires the application of a force that is greater in magnitude to that of adhesion. Fluid shear forces have been shown to be a simple method for cell detachment. Although this is a local and simple method of cell release, excessive exposure to fluid shear results in cell damage and reduction in viability. An alternative approach is to cleave the protein ligand that is bound to the capture surface using enzymes, such as trypsin. However, enzymatic exposure can cause morphological changes due to a disruption of the cell membrane and glycocalyx, leading to losses in cellular activity. Furthermore, enzymatic digestion has been shown to directly affect both the behavior and chemical makeup of the cells themselves.

These limitations illustrate the need to establish a general technique to capture and release biological materials, such as cells, without extensive physical or chemical perturbations to the cell environment. There remains a need for surfaces and gels that have high specificity for particular cells and that allow the release of captured cells without altering the behavior and makeup of the cells.

In addition to biological separation, there is a critical need for biological purification technologies that also demonstrate high recovery and yield. Current automation platforms have limited recovery due to inherent limitations of the chemical composition within their process reagents and/or inefficiencies in the process workflows. These limited recoveries and yields have greatly hindered the study of rare cells, proteins, and nucleic acids within heterogeneous tissue samples. The purification of these targeted moieties would allow the advancement of new therapies, new fundamental biological understandings, and development of personalized theranostics. Although there has been some work on automation technologies that have been implemented in current workflows in an attempt to increase the purification yield, there is a need for a low non-specific binding chemistry within automation components.

SUMMARY OF THE INVENTION

In general, the invention features shaped articles having a structure and a hydrogel coating that are useful in the separation of targets from a sample.

In one aspect, the invention features a shaped article including a structure with a hydrogel coating. The hydrogel coating includes alginic acid conjugated to a polyalkylene oxide, e.g., polyethylene oxide (PEG), and a binding moiety. In specific embodiments, the hydrogel coating on the structure is sized and shaped to fit in a well in a microtiter plate, e.g., with 24, 96, 384, or 1536 wells, and the coating does not cover the entire exterior of the surface. In other embodiments, the structure includes a plurality of hydrogel coatings thereon, each of which may be the same or different. In further embodiments, the structure includes a tubular portion, e.g., a capillary tube or a pipette tip, wherein the hydrogel coating is on the interior, exterior, or both of the portion.

In embodiments of any of the above aspects, the hydrogel is gelled by crosslinking alginic acid molecules by a cation, e.g., $Li^+$, $Mg^{2+}$, $Ca^{2+}$, $Sr^{2+}$, $Ba^{2+}$, $Zn^{2+}$, $Cu^{2+}$, or $Al^{3+}$, preferably $Ca^{2+}$.

Examples of binding moieties include an antibody or antigen-binding fragment thereof, a peptide, an oligonucleotide, a receptor, or a ligand. A binding moiety that is an antibody or antigen binding fragment thereof may be a monoclonal antibody or antigen-binding fragment thereof, an Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv (($scFv'$)$_2$) molecule, a domain antibody, a diabody, a triabody, an affibody, a domain antibody, a SMIP, a nanobody, a Fv fragment, a Fab fragment, a F(ab')$_2$ molecule, and a tandem scFv (taFv) fragment. Specific binding moieties include an anti-CD4 antibody, anti-CD8 antibody, anti-CD15 antibody, anti-CD20 antibody, anti-CD24 antibody, anti-CD30 antibody, anti-CD31 antibody, anti-CD33 antibody, anti-CD34 antibody, anti-CD44 antibody, anti-CD45 antibody, anti-CD52 antibody, anti-CD90 antibody, anti-CD117 antibody, anti-CD133 antibody, anti-CD142 antibody, anti-CD146 antibody, anti-CD184 antibody, anti-CD200 antibody, anti-CD318 antibody, anti-A2B5 antibody, anti-c-Kit antibody, anti-EGFR antibody, anti-FGFR3 antibody, anti-FGFR4 antibody, anti-Flk1 antibody, anti-Frizzled-9 antibody, anti-GLAST antibody, anti-Glut1 antibody, anti-HER2 antibody, anti-α4 integrin antibody, anti-N-CAM antibody, anti-Notch-1 antibody, anti-Notch-2 antibody, anti-Sca1 antibody, anti-SIPRA antibody, anti-somatostatinR1 antibody, anti-somatostatinR2 antibody, anti-somatostatinR3 antibody, anti-somatostatinR4 antibody, anti-somatostatinR5 antibody, anti-SSEA-3 antibody, anti-SSEA-4 antibody, an anti-GCPR antibody, or anti-Stro-1 antibody, or antigen binding fragment thereof. A binding moiety that is a peptide may be TNF-α, IL-1β, IL-2, IL6, IL10, α4-integrin, CD15 or an extracellular fragment thereof, CD20 or an extracellular fragment thereof, CD30 or an extracellular fragment thereof, or VEGF. Other binding moieties include biotin, avidin, streptavidin, protein A, and protein G.

Exemplary structures include a polymer, ceramic, glass, or metal. Examples of polymers include polyethylene, polypropylene, polybutene, polybutadiene, polystyrene, polyacrylonitrile, polycarbonate, PEEK, or a blend or a copolymer thereof. Examples of metals include aluminum, titanium, steel, copper, or zinc.

In certain embodiments of any aspect of the invention, the structure includes a plurality of members, and the hydrogel coating is on each member. The hydrogel coatings may be the same or different, e.g., by including the same or different alginic acid, polyalkylene oxide, e.g., PEG, or binding moiety. In specific embodiments, the plurality of members is arranged for placement in individual wells of a microtiter plate, e.g., with 24, 96, 384, or 1536 wells, e.g., in a single row or column.

In other embodiments of any aspect of the invention, the surface of the structure adjacent to the hydrogel coating is hydrophobic.

In a related aspect, the invention features a method of capturing a target including providing a shaped article of the invention; contacting the hydrogel coating with a first liquid containing the target under conditions allowing for binding of the target to the binding moiety; and removing the hydrogel coating from contact with the first liquid, thereby capturing the target. The method may further include contacting the hydrogel coating with a second liquid containing a release agent that releases the target from the shaped article, e.g., $H^+$ or $OH^-$ (i.e., a pH change) or a chelating agent for a cation crosslinking the alginic acid, e.g., EDTA, EGTA, sodium citrate, BAPTA, crown ether, cryptand, phenanthroline sulfonate, dipyridyl sulfonate, dioxane, DME, diglyme, or triglyme.

In certain embodiments, the shaped article is provided by contacting the structure with a third liquid containing alginic acid and optionally polyalkylene oxide, e.g., PEG, and binding moiety, so that the third liquid coats the structure, and contacting the structure coated with the third liquid with cations to crosslink the alginic acid to form the hydrogel coating. In this embodiment, the alginic acid in the third liquid may be conjugated to the polyalkylene oxide, e.g., PEG, and the binding moiety, or the polyalkylene oxide, e.g., PEG, and/or binding moiety may be conjugated to the alginic acid after gelation.

In certain embodiment, the hydrogel coating is contacted with the first liquid in a well of a microtiter plate, e.g., with 24, 96, 384, or 1536 wells. In other embodiments, the first liquid is agitated during contact with the hydrogel coating, e.g., by movement of the shaped article. In other embodiments, the shaped article includes a lumen via which the first composition can be drawn in and expelled.

In another aspect, the invention features a method of producing a shaped article by contacting a structure with a first liquid containing alginic acid and optionally polyalkylene oxide, e.g., PEG, and binding moiety, so that the first liquid coats the structure, and contacting the structure coated with the first liquid with cations to crosslink the alginic acid to form a hydrogel coating on the structure, thereby forming the shaped article. In certain embodiments, the two contacting steps occur in different wells of a microtiter plate, e.g., with 24, 96, 384, or 1536 wells.

DETAILED DESCRIPTION OF THE INVENTION

Figure 1:
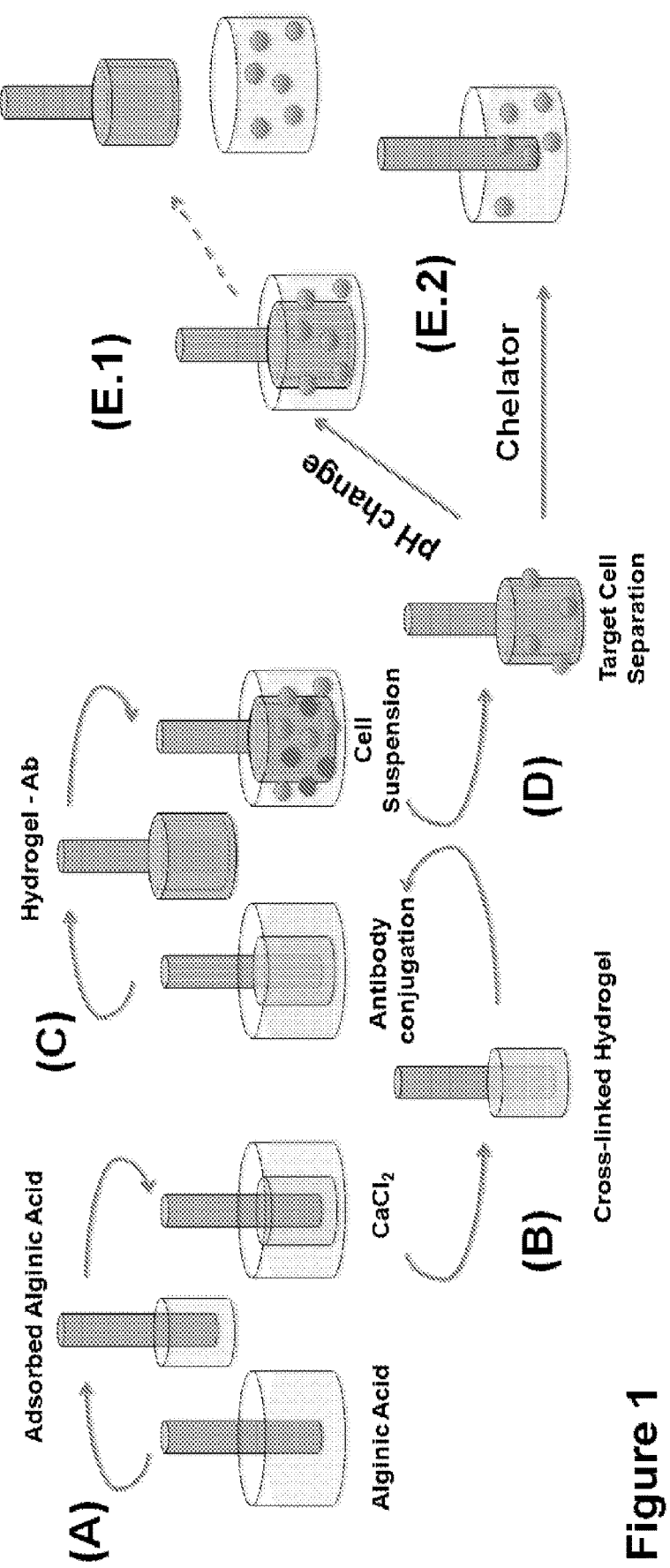
FIGS. 1A-1E.2 are schemes showing the sequence of coating a structure with alginic acid conjugated to PEG (A) and crosslinking the alginic acid (B); conjugation of a binding moiety, e.g., an antibody, to the hydrogel (C); contacting the hydrogel with a sample, e.g., a cell suspension, to separate target cells (D); and optionally releasing the target cells by pH change (E.1) or chelation (E.2).

The disclosure provides shaped articles having a structure with a hydrogel coating of alginic acid conjugated to a polyalkylene oxide, e.g., polyethylene oxide (PEG), and a binding moiety, methods of forming such articles, and methods of using such articles for separation of targets from a sample. The hydrogel is typically formed in the presence of cations. Such hydrogels are capable of easily dissolving in the presence of chelators.

Alginic acid provides a foundation for an improved separation. In the presence of a cation, e.g., calcium, alginic acid crosslinks and solidifies. Polyalkylene oxide, e.g., PEG, provides nonspecific binding or other beneficial properties to the hydrogel. An article having an alginic acid hydrogel including binding moieties can be dipped or otherwise contacted with a sample, where target present in the sample will bind to the hydrogel. Once target binds, the hydrogel can be removed from the sample and dissolved using a chelator, e.g., to release the target or leave the uncoated structure available for reuse. In this context, the article can be used to purify a composition by positive or negative selection. For example, a desired target can bind to the binding moiety and be removed from the sample for further study or manipulation. Alternatively, the sample may be purified by using the hydrogel to remove a substance from the sample, leaving behind a purified sample.

Shaped Articles

The structure may be formed of any suitable material, such as a polymer, (e.g., polyethylene, polypropylene, polybutene, polybutadiene, polystyrene, polyacrylonitrile, polycarbonate, PEEK, or a blend or a copolymer thereof), ceramic, glass, or metal (e.g., aluminum, titanium, steel, copper, or zinc). The structure may also include combinations of these materials. The shape of the structure may be any suitable shape, such as elongated like a wire or tubular, i.e., having a lumen connectable to a pressure source. The hydrogel coating will typically be on the outer surface of the structure, although a structure having a lumen may include the coating on the interior of the lumen, the exterior of the lumen, or both. Suitable tubular structures include glass capillary tubes and micropipette tips. Structures or portions to be coated with the hydrogel may be textured or porous to allow greater surface area for adhesion of the hydrogel. Structures may also include larger voids, e.g., through holes, to increase the surface area for adhesion of the hydrogel. Smooth and solid structures are also of use in the invention.

In preferred embodiments, the structure is sized and shaped so that the hydrogel coating fits in a well in a microtiter plate e.g., with 6, 24, 96, 384, or 1536 wells. In other embodiments, the structure of the shaped article is only partially coated with the hydrogel. In such embodiments, the structure may include a portion, e.g., having a hydrophobic coating, a different material, or a smooth surface texture, adjacent to the location where the hydrogel coating is placed and that is not wet by aqueous liquids. Such a portion can be used to define the location of the structure where the liquid including alginic acid will wet the structure and thus where the hydrogel will form. Structure may also include a plurality of members, e.g., to allow formation and/or use of multiple hydrogel coatings in one shaped article. Such members may be spaced, e.g., to fit into wells in one column or row of a microtiter plate, e.g., with 6, 24, 96, 384, or 1536 wells. In another embodiment, multiple hydrogels, e.g., distinguished by different binding moieties, can be disposed on a single structure, e.g., a single wire or tube. Structures with multiple hydrogels can be contacted with a single sample to separate multiple targets in spatially distinct locations on the shaped article.

In certain embodiments, the structure is coated with hydrogel and stored prior to use in a separation. In other embodiments, the shaped article is formed in a sequence of steps preceding its use in separation.

Methods

A structure may be coated, e.g., by dipping, painting, or spraying, with a liquid alginic acid composition and then contacted with cations for crosslinking, e.g., by dipping, painting, or spraying. In producing the coating, the alginic acid may be conjugated to the polyalkylene oxide, e.g., PEG, and/or the binding moiety and in a liquid composition prior to coating. Alternatively, the polyalkylene oxide, e.g., PEG, and/or binding moiety may be conjugated to the alginic acid after the alginic acid is crosslinked on the structure. In certain embodiments, the alginic acid is conjugated to the polyalkylene oxide, e.g., PEG, prior to gelation, and the binding moiety is conjugated after gelation. Once coated with a liquid including the alginic acid, the structure can be removed from the liquid and contacted with cations to crosslink the hydrogel, e.g., by dipping in another liquid. Alternatively, cations can be added to the alginic acid liquid while the structure is in contact with it. Microtiter plates, e.g., with 6, 24, 96, 384, or 1536 wells, provide a commercially available platform for housing liquids for dipping structures in sequence to form hydrogels and also to contact the hydrogel formed with a sample. Other arrangements of containers can be used for this purpose Once formed, the hydrogel, or portion thereof, of a shaped article can be contacted with a sample to bind and separate a target (or multiple targets).

FIG. 1 is a scheme of using shaped articles of the invention. In FIG. 1A, a structure is dipped into a liquid including alginic acid conjugated to polyalkylene oxide, e.g., PEG. The liquid wets or adsorbs to the structure, which is then dipped in a solution of cation, e.g., $Ca^{2+}$, to produce a crosslinked hydrogel on the structure (1A). The hydrogel is then dipped in a solution of binding moiety, e.g., antibody, which conjugates to the hydrogel (1B). The hydrogel is then dipped in a cell suspension, and target cells bind to the hydrogel (1C). The hydrogel with bound cells is removed from the sample (1D), and the cells can be released from the hydrogel by disrupting the binding to the binding moiety, e.g., by a pH change (1E.1), or by dissolving the gel (1E.2).

Figure 2:
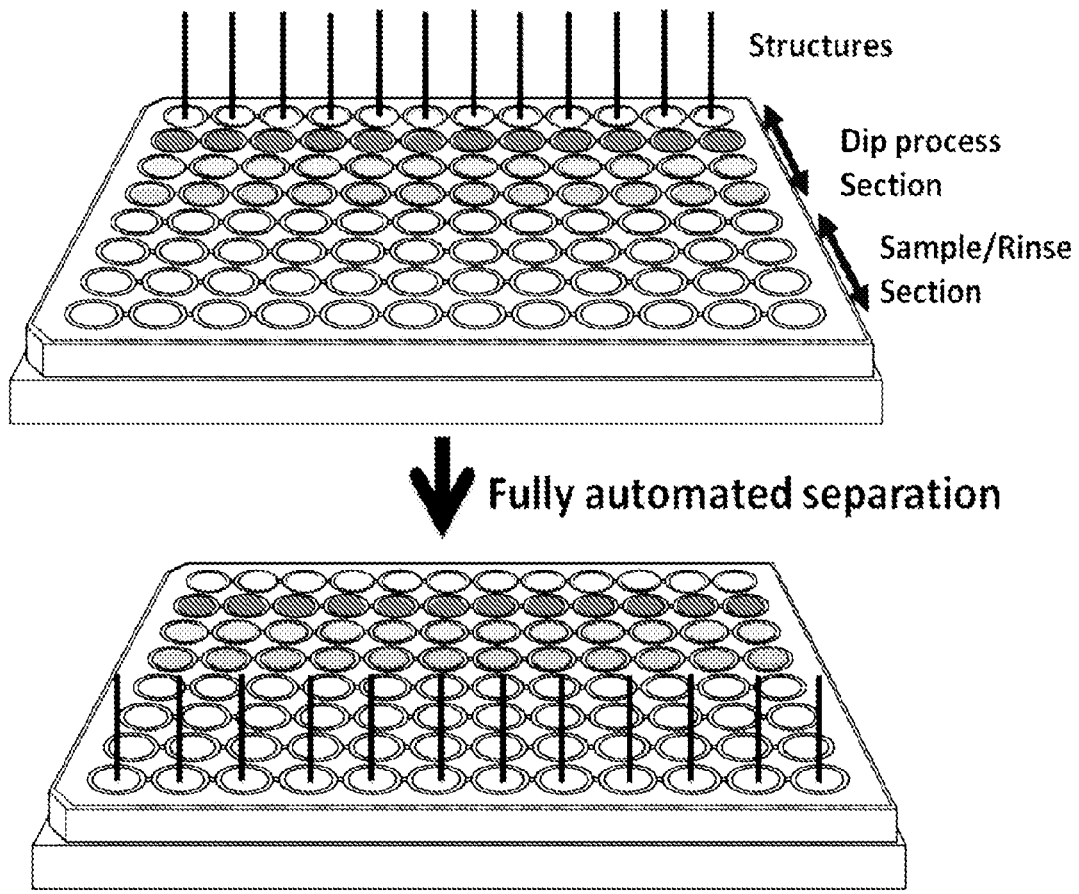
FIG. 2 is a scheme showing the formation and use of a shaped article of the invention in a sequence of steps carried out in a microtiter plate.

FIG. 2 is a scheme showing the formation of a shaped article and the subsequent use of the article in a single sequence of steps. A series of structures (or a single structure with multiple members) is dipped into a row of wells in a microtiter plate, where the row contains a liquid alginic acid composition. The structure is then removed and dipped in the second row containing cations to crosslink the hydrogel and form a shaped article. The shaped article is then removed and dipped in the third row containing a binding moiety that conjugates to the hydrogel. The shaped article is then removed and dipped in the fourth row to rinse unbound reagents from the hydrogel. The shaped article is then dipped in the fifth row containing a sample containing targets that bind to the binding moiety. The shaped article may then be dipped in rows for rinsing, release of the target, contact with further samples, or release of target from the binding moiety or dissolution of the hydrogel. Additional reagents may also be employed. For example, prior to dipping in the liquid alginic acid composition, the structure or structures may be dipped in one or more reagents to clean or otherwise prepare the structure for adhesion of the hydrogel. Additional rows may also be employed to conjugate the polyalkylene oxide, e.g., PEG, with the alginic acid after gelation of the alginic acid. In addition, although illustrated with a microtiter plate, any collection of liquid containers may be employed, and such containers may or may not be physically connected to one another. The process shown in FIG. 2 may be manual or fully automated. Use of the invention for separation or purification can be scaled to a production scale, e.g., to aid in purification of therapeutic biologics.

The structure or shaped article may be agitated during the process of coating the structure, crosslinking the hydrogel, conjugating a polyalkylene oxide, e.g., PEG, and/or binding moiety, contacting the hydrogel with sample, or contacting the hydrogel with an agent to release the target or dissolve the hydrogel. Such agitation may be performed by any suitable method known in the art. For example, liquids into which the structure or shaped article is dipped can be stirred (e.g., with a magnetic stir bar), sonicated, shaken, or aerated to provide stirring. Alternatively, the structure or shaped article can be moved, e.g., vertically, horizontally, rotationally, or combinations thereof, in the liquid to agitate it. When a structure has a lumen connected to a suction source, e.g., a pipettor, liquid can be drawn in and out of the lumen to agitate the liquid.

Hydrogel

Hydrogels of the invention are formed from alginic acid conjugated to a polyalkylene oxide, e.g., PEG, and a binding moiety, e.g., as generally described in WO 2012/106658. A reference to alginic acid is also a reference to a salt form, e.g., sodium alginate, unless otherwise noted. Suitable alginic acid is 20 kDa medium viscosity. Polyalkylene oxides, e.g., PEG and polypropylene oxide, are known in the art. Linear or branched, e.g., 4-arm or 8-arm, polyalkylene oxides, e.g., PEG, may be employed. The polyalkylene oxide, e.g., PEG, preferably has a molecular weight between 10 kDa and 20 kDa. An exemplary ratio of polyalkylene oxide, e.g., PEG, to alginic acid is 1:2 by weight.

Alginic acid naturally possess multiple carboxyl groups that provide convenient groups for conjugation to polyalkylene oxide, e.g., PEG, and/or binding moieties. The polyalkylene oxide, e.g., PEG, and binding moiety will naturally possess or be modified to possess an appropriate group to conjugate to a carboxyl group. Suitable groups include amine groups, which are often found in binding moieties that include amino acids or can be introduced into binding moieties and polyalkylene oxides, e.g., PEG. For example, amine-terminated polyalkylene oxide, e.g., PEG, can be employed. In other embodiments, a linker may be use to conjugate appropriate groups on the polyalkylene oxide, e.g., PEG, or binding moiety to carboxyl groups on the alginic acid. In the hydrogel, a single polyalkylene oxide, e.g., PEG, may be conjugated to one or more alginic acid molecules. When a polyalkylene oxide binds to more than one alginic acid, the number of such crosslinks in the composition may or may not be sufficient to form a gel. The binding moiety can bind to either the alginic acid directly or to a polyalkylene oxide, e.g., PEG, bound to alginic acid.

The hydrogel forms by crosslinking of the alginic acid with a cation, e.g., $Li^+$, $Mg^{2+}$, $Ca^{2+}$, $Sr^{2+}$, $Ba^{2+}$, $Zn^{2+}$, $Cu^{2+}$, or $Al^{3+}$. A preferred cation is $Ca^{2+}$. Gelation of hydrogels of the invention may be reserved by contact with a chelator for the cation, e.g., EDTA, EGTA, sodium citrate, BAPTA, crown ether, cryptand, phenanthroline sulfonate, dipyridyl sulfonate, dioxane, DME, diglyme, or triglyme.

Binding Moiety

Binding moieties are those that bind to a particular target with specificity. Suitable binding moieties, as well as methods of conjugating such moieties to alginic acid or polyalkylene oxide, e.g., PEG, are known in the art. Examples of binding moieties include an antibody or antigen-binding fragment thereof, a peptide, a polynucleotide (e.g., an aptamer or specific sequence for hybridization), a receptor, a ligand, or a charged polymer. Typically, the target of the binding moiety will naturally be part of the target, but targets may be modified for binding to a binding moiety. For example, biotin-avidin or streptavidin or histidine tags and nickel or cobalt ions bound to a chelator may be used. Other binding moieties include protein A and protein G for antibodies. In certain embodiments, the binding interaction between the binding moiety and the target may be disrupted, e.g., by a change in pH or salt concentration or addition of a denaturant, e.g., a detergent, reducing agent, or oxidizing agent, or cleaving agent, e.g., protease or nuclease.

Preferred targets are specific cells or fragments thereof, viruses or fragments thereof, nucleic acids, proteins, lipids, and metabolites.

An antibody or antigen binding fragment thereof is, for example, a monoclonal antibody or antigen-binding fragment thereof, an Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')$_2$) molecule, a domain antibody, a diabody, a triabody, an affibody, a domain antibody, a SMIP, a nanobody, a Fv fragment, a Fab fragment, a F(ab')$_2$ molecule, and a tandem scFv (taFv) fragment. Specific antibodies include an anti-CD4 antibody, anti-CD8 antibody, anti-CD15 antibody, anti-CD20 antibody, anti-CD24 antibody, anti-CD30 antibody, anti-CD31 antibody, anti-CD33 antibody, anti-CD34 antibody, anti-CD44 antibody, anti-CD45 antibody, anti-CD52 antibody, anti-CD90 antibody, anti-CD117 antibody, anti-CD133 antibody, anti-CD142 antibody, anti-CD146 antibody, anti-CD184 antibody, anti-CD200 antibody, anti-CD318 antibody, anti-A2B5 antibody, anti-c-Kit antibody, anti-EGFR antibody, anti-FGFR3 antibody, anti-FGFR4 antibody, anti-Flk1 antibody, anti-Frizzled-9 antibody, anti-GLAST antibody, anti-Glut1 antibody, anti-HER2 antibody, anti-α4 integrin antibody, anti-N-CAM antibody, anti-Notch-1 antibody, anti-Notch-2 antibody, anti-Sca1 antibody, anti-SIPRA antibody, anti-somatostatinR1 antibody, anti-somatostatin R2 antibody, anti-somatostatin R3 antibody, anti-somatostatin R4 antibody, anti-somatostatinR5 antibody, anti-SSEA-3 antibody, anti-SSEA-4 antibody, anti-GCPR antibody, or anti-Stro-1 antibody. Antigen binding fragments of such antibodies are also suitable binding moieties. Examples of peptides include TNF-α, IL-1β, IL-2, IL6, IL10, α4-integrin, CD15 or an extracellular fragment thereof, CD20 or an extracellular fragment thereof, CD30 or an extracellular fragment thereof, or VEGF.

A single hydrogel may include multiple binding moieties, e.g., when one or more targets are desired in a single sample. In embodiments, where the structure includes a plurality of hydrogels, individual hydrogels may have the same or different binding moieties conjugated to them.

Samples

Hydrogels of the invention may be used to separate targets from any suitable liquid sample (or sample that has been dissolved or suspended in liquid). Samples may include bodily fluids, e.g., blood, plasma, serum, urine, saliva, lymph, spinal fluid, bile, mucus, tears, and amniotic fluid. Other samples include cell or viral culture and environmental samples (e.g., air, surface, or water samples).

EXAMPLES

Figure 3:
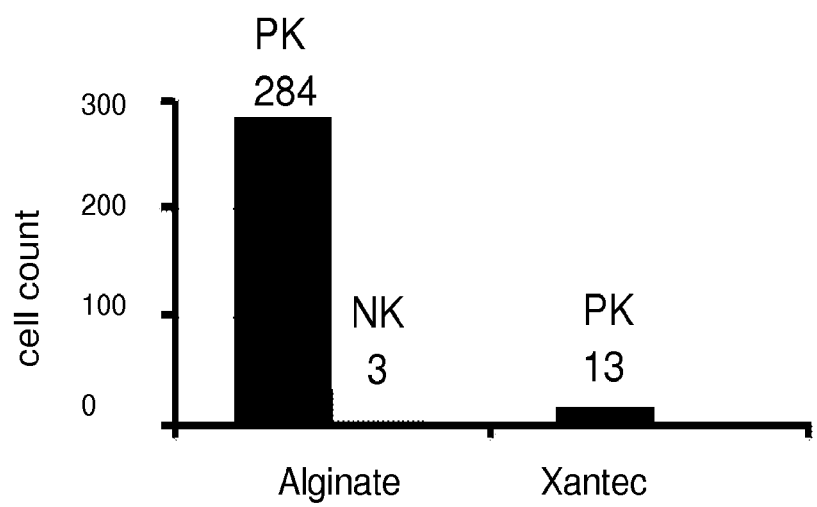
FIG. 3 is a graph comparing the capture of cells using a hydrogel of the invention to Xantec polymer coatings.
Figure 4:
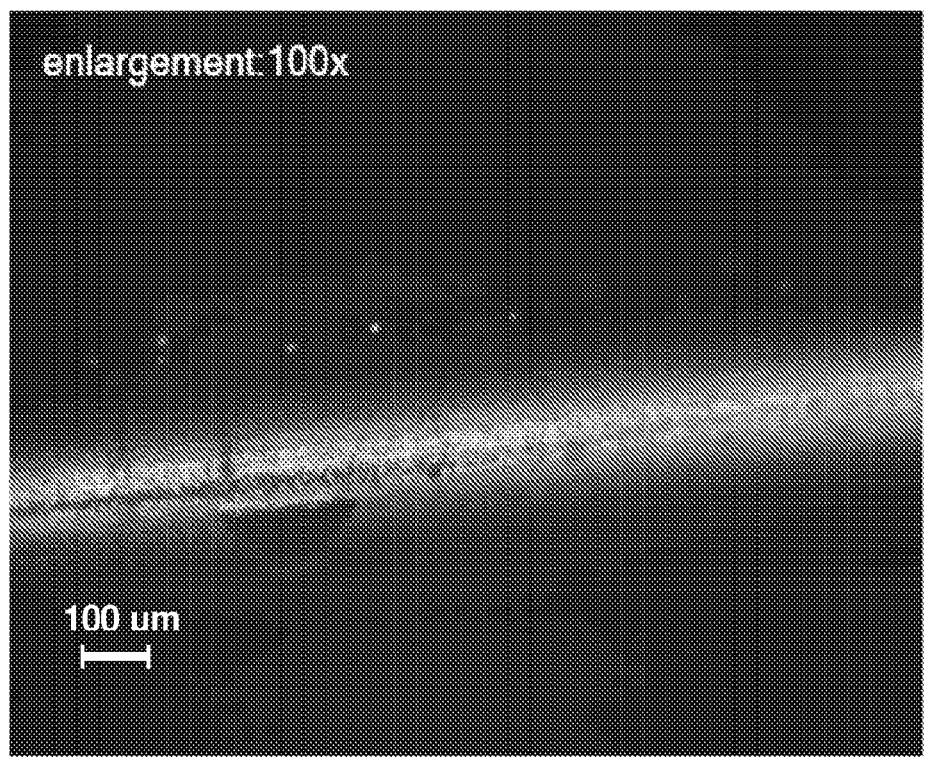
FIG. 4 is a micrograph of cells bound to a hydrogel of the invention coated on a wire.

Stainless steel wires were coated with an alginate—PEG solution and crosslinked with a 1 mg/mL solution of Ca$^{2+}$. The divalent cations ionically bound the alginic acid and formed a solid coating around the wire (as shown in FIG. 4). The resulting coating was 200-500 microns in thickness homogenously around the wire. Antibodies against EpCAM proteins (100 µg/mL) on circulating tumor cells were chemical conjugated to the hydrogel for the purposes of selectively binding MCF-7 cancer cells. The hydrogel coating of the invention was compared against a propriety polymer coating (Xantec) (FIG. 3). Both the hydrogel coated and Xantec polymer coated stainless steel wires were placed in a homogenous suspension of MCF-7 breast cancer cells in phosphate buffer solution for 30 minutes with slow rotational mixing. The wires were removed and rinsed prior to staining for cell nuclei via DAPI staining. As shown in FIG. 4, cells can be visualized and counted under a fluorescence microscope. The hydrogel coating of the invention provided significantly higher recoveries versus the Xantec polymer coating as shown in FIG. 3.

FIG. 3: Comparative recovery data of capture MCF-7 cells of polymer coating technology (Xantec) against the hydrogel coating of the invention. The purifications from the suspension containing a known concentration of MCF-7 cells were performed with an anti-EpCAM (PK) coating and a un-functionalized (NK) bare hydrogel coating.

FIG. 4: Fluorescent image demonstrating compositions of mentioned hydrogel bound to a medical grade stainless steel wire. Compositions were functionalized with anti-EpCAM and captured MCF-7 cells to the surface stained with DAPI.

Other Embodiments

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A shaped article comprising a structure and a hydrogel coating thereon, wherein the structure comprises a plurality of members and the hydrogel coating is on each member, wherein the plurality of members are sized and spaced such that each member fits in a separate well in one column or row of a microtiter plate, wherein the hydrogel coating comprises alginic acid conjugated to a polyalkylene oxide and a binding moiety, and wherein the coating on each member does not cover the entire surface of the member.

2. The shaped article of claim 1, wherein the alginic acid molecules in the hydrogel are crosslinked by a cation.

3. The shaped article of claim 2, wherein the cation is Li$^+$, Mg$^{2+}$, Ca$^{2+}$, Sr$^{2+}$, Ba$^{2+}$, Zn$^{2+}$, Cu$^{2+}$, or Al$^{2+}$.

4. The shaped article of claim 1, wherein the polyalkylene oxide is polyethylene oxide.

5. The shaped article of claim 1, wherein the binding moiety is an antibody or antigen-binding fragment thereof, a peptide, an oligonucleotide, a receptor, or a ligand.

6. The shaped article of claim 5, wherein the binding moiety is an antibody or antigen-binding fragment thereof.

7. The shaped article of claim 6, wherein the binding moiety is an anti-CD4 antibody, anti-CD8 antibody, anti-CD15 antibody, anti-CD20 antibody, anti-CD24 antibody, anti-CD30 antibody, anti-CD31 antibody, anti-CD33 antibody, anti-CD34 antibody, anti-CD44 antibody, anti-CD45 antibody, anti-CD52 antibody, anti-CD90 antibody, anti-CD117 antibody, anti-CD133 antibody, anti-CD142 antibody, anti-CD146 antibody, anti-CD184 antibody, anti-CD200 antibody, anti-CD318 antibody, anti-A2B5 antibody, anti-c-Kit antibody, anti-EGFR antibody, anti-FGFR3 antibody, anti-FGFR4 antibody, anti-Flk1 antibody, anti-Frizzled-9 antibody, anti-GLAST antibody, anti-Glut1 antibody, anti-HER2 antibody, anti-α4 integrin antibody, anti-N-CAM antibody, anti-Notch-1 antibody, anti-Notch-2 antibody, anti-Sca1 antibody, anti-SIPRA antibody, anti-somatostatinR1 antibody, anti-somatostatinR2 antibody, anti-somatostatinR3 antibody, anti-somatostatinR4 antibody, anti-somatostatinR5 antibody, anti-SSEA-3 antibody, anti-SSEA-4 antibody, an anti-GPCR antibody, or anti-Stro-1 antibody, or antigen binding fragment thereof.

8. The shaped article of claim 5, wherein the binding moiety is a peptide.

9. The shaped article of claim 8, wherein the peptide is TNF-α, IL-1β, IL-2, IL6, IL10, α4-integrin, CD15 or an extracellular fragment thereof, CD20 or an extracellular fragment thereof, CD30 or an extracellular fragment thereof, or VEGF.

10. The shaped article of claim 1, wherein the structure comprises a polymer, ceramic, glass, or metal.

11. The shaped article of claim 1, wherein the microtiter plate has 24, 96, 384, or 1536 wells.

12. The shaped article of claim 1, wherein the structure comprises a tubular portion, and the hydrogel coating is on the interior, exterior, or both of the portion.

13. The shaped article of claim 12, wherein the structure comprises a capillary tube or a pipette tip.

14. The shaped article of claim 1, wherein the surface of the structure adjacent to the hydrogel coating is hydrophobic.

15. A method of capturing a target, the method comprising:
(a) providing a shaped article comprising a structure and a hydrogel coating thereon, wherein the structure comprises a plurality of members and the hydrogel coating is on each member, wherein the plurality of members are sized and spaced such that each member fits in a separate well in one column or row of a microtiter plate, and wherein the hydrogel coating comprises alginic acid conjugated to a polyalkylene oxide and a binding moiety;
(b) contacting the hydrogel coating with a first liquid comprising the target under conditions allowing for binding of the target to the binding moiety; and
(c) removing the hydrogel coating from contact with the first liquid, thereby capturing the target.

16. The method of claim 15, further comprising contacting the hydrogel coating with a second liquid comprising a release agent that releases the target from the shaped article.

17. The method of claim 16, wherein the release agent is $H^+$ or $OH^-$.

18. The method of claim 15, wherein the alginic acid molecules in the hydrogel are crosslinked by a cation, and the release agent is a chelating agent for the cation.

19. The method of claim 18, wherein the chelating agent is EDTA, EGTA, sodium citrate, BAPTA, crown ether, cryptand, phenanthroline sulfonate, dipyridyl sulfonate, dioxane, DME, diglyme, or triglyme.

20. The method of claim 15, wherein step (b) occurs in a well of a microtiter plate.

21. The method of claim 15, wherein during step (b), the first liquid is agitated.

22. The method of claim 21, wherein the first composition is agitated by movement of the shaped article.

23. The method of claim 21, wherein the shaped article comprises a lumen via which the first composition can be drawn in and expelled.

24. A method of producing the shaped article of claim 1, the method comprising the steps of: (a) contacting the structure with a first liquid comprising alginic acid conjugated to a polyalkylene oxide, so that the first liquid coats the structure, (b) contacting the structure coated with the first liquid with cations to crosslink the alginic acid to form a hydrogel coating on the structure, and (c) conjugating a binding moiety to the hydrogel coating, thereby forming the shaped article.

25. The method of claim 24, wherein steps (a), (b), and (c) occur in different wells of a microtiter plate.

26. The shaped article of claim 3, wherein the cation is $Ca^{2+}$.

27. The shaped article of claim 4, wherein the polyethylene oxide is a branched polyethylene oxide.

28. The shaped article of claim 27, wherein the polyethylene oxide is a 4-arm branched polyethylene oxide.

* * * * *

UNITED STATES PATENT AND TRADEMARK OFFICE
CERTIFICATE OF CORRECTION

PATENT NO. : 10,739,338 B2
APPLICATION NO. : 15/128488
DATED : August 11, 2020
INVENTOR(S) : Sean H. Kevlahan, Brian D. Plouffe and Jeffrey A. Zonderman Page 1 of 1

It is certified that error appears in the above-identified patent and that said Letters Patent is hereby corrected as shown below:

In the Claims

Claim 3, Column 8, Line 51 reads:
"$Mg^{2+}$, $Ca^{2+}$, $Sr^{2+}$, $Ba^{2+}$, $Zn^{2+}$, $Cu^{2+}$ or $Al^{2+}$."

Whereas it should read:
"$Mg^{2+}$, $Ca^{2+}$, $Sr^{2+}$, $Ba^{2+}$, $Zn^{2+}$, $Cu^{2+}$ or $Al^{3+}$."

Signed and Sealed this
Third Day of November, 2020

Andrei Iancu
*Director of the United States Patent and Trademark Office*